(12) United States Patent
Loezos et al.

(10) Patent No.: US 7,015,174 B2
(45) Date of Patent: Mar. 21, 2006

(54) MAINTAINING MOLECULAR SIEVE CATALYTIC ACTIVITY UNDER WATER VAPOR CONDITIONS

(75) Inventors: Peter N. Loezos, Houston, TX (US); Shun Chong Fung, Bridgewater, NJ (US); Stephen Neil Vaughn, Kingwood, TX (US); Kenneth Ray Clem, Humble, TX (US); James H. Beech, Kingwood, TX (US); Nicolas P. Coute, Houston, TX (US); Marcel Johannes Janssen, Kessel-Lo (BE); Luc Roger Marc Martens, Meise (BE); Karl G. Strohmaier, Port Murray, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 250 days.

(21) Appl. No.: 10/600,123

(22) Filed: Jun. 20, 2003

(65) Prior Publication Data

US 2004/0260140 A1    Dec. 23, 2004

(51) Int. Cl.
*B01J 29/02* (2006.01)
*B01J 27/18* (2006.01)
*B01J 27/182* (2006.01)

(52) U.S. Cl. ...................................... 502/214; 502/208
(58) Field of Classification Search ................ 502/208, 502/241
See application file for complete search history.

(56) References Cited

U.S. PATENT DOCUMENTS

| 4,764,269 | A  | 8/1988  | Edwards et al. ............ 208/120 |
| 5,185,310 | A  | 2/1993  | Degnan et al. ............. 502/214 |
| 5,248,647 | A  | 9/1993  | Barger ....................... 502/214 |
| 5,663,471 | A  | 9/1997  | Kvisle et al. ............... 585/639 |
| 6,225,254 | B1 | 5/2001  | Janssen et al. ............. 502/214 |
| 6,245,703 | B1 | 6/2001  | Kuechler et al. ............. 502/22 |
| 6,316,683 | B1 | 11/2001 | Janssen et al. ............. 585/640 |
| 6,441,261 | B1 | 8/2002  | Kuechler et al. ........... 585/639 |
| 6,503,863 | B1 | 1/2003  | Fung et al. ................. 502/214 |

FOREIGN PATENT DOCUMENTS

EP    0 359 841    3/1990

OTHER PUBLICATIONS

Briend et al., "Influence of the Choice of Template on the Short-and-Long-Term Stability of SAPO Zeolite," *J. Phys. Chem.*, vol. 99, pp. 8270-8276, (1995), no month.

Simonot-Grange et al., "Contribution to the Study of Framework Modification of SAPO-34 and SAPO-37 upon water Adsorption by Thermgravimetry," *Thermchimica Acta*, vol. 329, pp. 77-82, (1999), no month.

Mees et al., "Improvement of the Hydrothermal Stability of SAPO-34," *Chem. Commun.*, vol. 1, pp. 44-45, (2003), no month.

*Primary Examiner*—Elizabeth D. Wood

(57) ABSTRACT

The invention is directed to methods for protecting metalloaluminophosphate molecular sieves, particularly silicoaluminophosphate (SAPO) molecular sieves, from loss of catalytic activity due to contact with a gas containing water. The methods of the invention provide procedures that enable activated sieve to contact water vapor, within a certain range of time, temperature, and water partial pressure conditions, before the sieve becomes substantially deactivated.

49 Claims, 1 Drawing Sheet

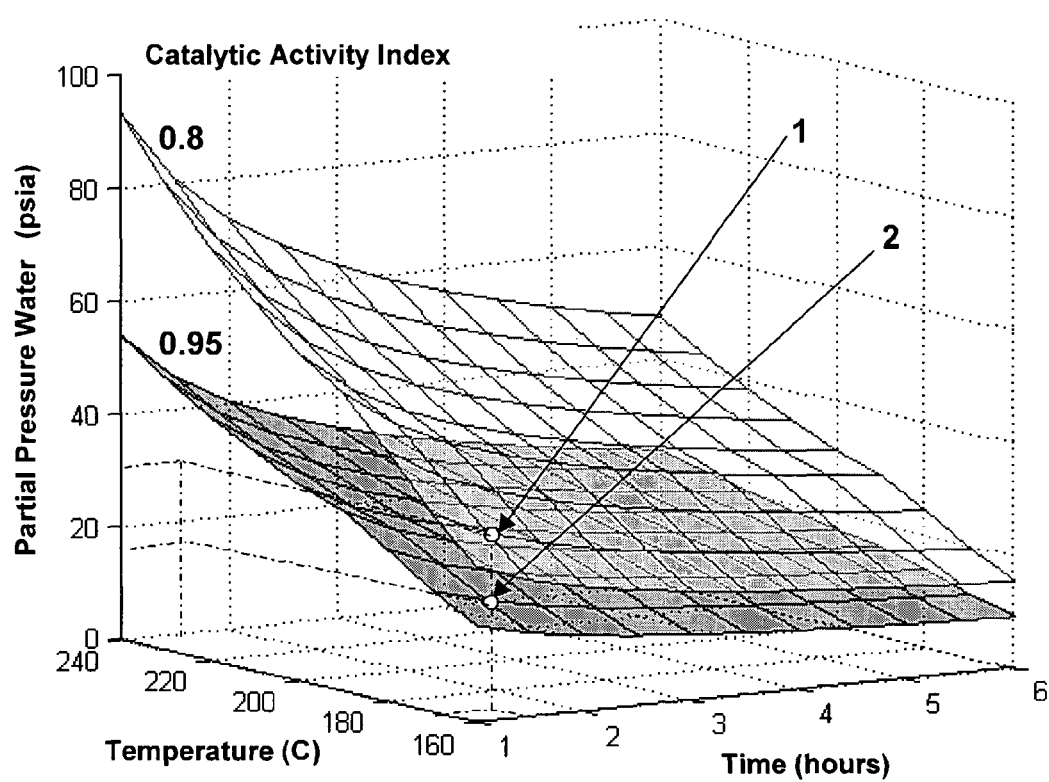
FIGURE

MAINTAINING MOLECULAR SIEVE CATALYTIC ACTIVITY UNDER WATER VAPOR CONDITIONS

FIELD OF THE INVENTION

This invention relates to methods of maintaining or protecting the catalytic activity of a molecular sieve. In particular, this invention relates to methods of maintaining or protecting the catalytic activity of a metalloaluminophosphate molecular sieve under water vapor or steaming conditions.

BACKGROUND OF THE INVENTION

Molecular sieves are generally derived from alumina silicate materials and contain a pore system, which is a network of uniform pores and empty cavities. These pores and cavities catch molecules that have a size equal to or less than the size of the pores and cavities, and repel molecules of a larger size.

The pores and cavities of molecular sieves are formed as a result of adding template materials during the molecular sieve manufacturing process. During the formation of the molecular sieves themselves, a lattice type chemical structure is formed from the alumina silicate type materials. This lattice type structure essentially wraps around the template material, with the template material acting as a means of forming the pore structure within the molecular sieve. The resulting molecular sieve may be combined with other components for the benefit of adjusting various properties of the molecular sieve or to form larger particles.

To make the molecular sieve suitable for use, the template must be removed so that the pores and cavities are open to catch molecules, either for the purpose of adsorbing the molecules from the environment or to react the molecules to form a desired product. The reaction occurs when the molecules come into contact with catalytic sites located within the pore system, particularly within one or more of the empty cavities or cages as sometimes called.

The template is conventionally removed from the molecular sieve by calcining or burning out the template. An elution process can also be used to remove the template, although calcination is preferred. Once the template is removed, the molecular sieve is considered to be activated or ready for use. The activated molecular sieve has its pore system, including the empty cavities or cages open to the immediate environment, and ready for use.

Activated metalloaluminophosphate molecular sieves that have catalytic sites within their microporous structure, e.g., silicoaluminophosphate (SAPO) molecular sieves, have been found to be sensitive to moisture. In general, significant exposure of the activated molecular sieves to moisture has been found to deactivate the catalytic activity of the molecular sieves. Unfortunately, methods of protecting activated metalloaluminophosphate molecular sieves against the harmful effects of moisture are limited.

U.S. Pat. No. 6,316,683 B1 (Janssen et al.) discloses a method of protecting catalytic activity of a SAPO molecular sieve by shielding the internal active sites of the molecular sieve from contact with moisture. The template itself can serve as the shield, or an anhydrous blanket can serve as a shield for an activated sieve that does not include template. It is desirable to shield the active sites, because activated SAPO molecular sieves will exhibit a loss of catalytic activity when exposed to moisture.

U.S. Pat. No. 4,764,269 (Edwards et al.) discloses a method of protecting SAPO-37 catalyst from deactivating as a result of contact with moisture. The catalyst is maintained under storage conditions such that the organic template component of the molecular sieve is retained in the SAPO-37 molecular sieve, until such time as the catalyst is placed into a catalytic cracking unit. When the catalyst is exposed to the FCC reaction conditions, wherein the reactor is operated at 400° to 600° C. and the regenerator operated at about 6000 to 850° C., the organic template is removed from the molecular sieve pore structure, and the catalyst becomes activated for the cracking of hydrocarbons. According to this procedure, there is little if any contact with moisture.

Mees et al., "Improvement of the Hydrothermal Stability of SAPO-34," *Chem. Commun.*, 2003, (1), 44–45, first published as an advance article on the web Nov. 22, 2002, discloses a method of protecting SAPO-34 molecular sieve, based on a reversible reaction of $NH_3$ with acid sites of the sieve. The method transforms a $H^+$-SAPO-34 into an $NH_4^+$-SAPO-34 in reversible way. The $NH_4^+$-SAPO-34 is said to be able to withstand severe steaming for an extended period of time without loss of structural integrity and acidity.

As new large scale, commercial production facilities, which use metalloaluminophosphate molecular sieves in the production process, continue to be implemented, protecting the activated metalloaluminophosphate molecular sieves from loss of catalytic activity as a result of contact with moisture continues to become an even greater challenge. It is a particular challenge in catalytic reaction systems where large scale operation will entail contacting the activated molecular sieve with water vapor, particularly at times of start-up, shut-down, or as a result of a system interruption or failure. During such times, it may be necessary to use steam to keep the reaction system heated or at appropriate catalyst bed densities. Even at higher temperature ranges, contact of the activated sieve with water vapor can result in sieve that has little to no catalytic activity, which means that the sieve would then be of essentially no commercial value.

SUMMARY OF THE INVENTION

In one aspect, this invention provides methods that assist in the protection of metalloaluminophosphate molecular sieves against loss of catalytic activity. These methods are particularly effective under certain conditions where activated molecular sieve is contacted with water vapor or steam. In one, embodiment, the activated metalloaluminophosphate molecular sieve is protected against loss of catalytic activity by contacting the molecular sieve with a gas containing water at a temperature above water critical temperature. In another embodiment, the molecular sieve is protected against loss of catalytic activity by contacting the molecular sieve with a gas containing water at a temperature below water critical temperature to maintain a desired or predetermined catalytic activity index.

In one embodiment, the invention provides a method of protecting activated metalloaluminophosphate molecular sieve from loss of catalytic activity, which comprises contacting the activated metalloaluminophosphate molecular sieve with a gas containing water at a temperature and water partial pressure effective to maintain the molecular sieve at a desirable or predetermined catalytic activity index (CAI), e.g., a CAI capable of converting hydrocarbon feed to desirable product. The catalytic activity index is represented by the formula:

$$CAI = \exp(f(T) * f(PP_{water})^{n} * alpha * t)$$

wherein
- t=time of contact of catalyst with water (hours)
- T=temperature at contact (° C.)
- $PP_{water}$=Partial Pressure of water in contact gas (psia)
- alpha=−0.071
- n=3.5
- $f(T)=\exp(ea(1/(T+273)-1/(T_o+273)))$
- ea =−5500° K
- $T_o$=200° C.
- $f(PP_{water})=(26.2*PP_{water}/P_{sat}+1.14)*0.175$, for T≧180° C. (453° K)
- $f(PP_{water})=((26.2+0.272*(180-T))*PP_{water}/P_{sat}+1.14)*0.175$, for 180° C. (453° K)>T≧150° C. (433° K)
- $P_{sat}$=Saturation pressure of water at T (psia).

In one embodiment, a desirable or predetermined catalytic activity index is a CAI of at least 0.7. Preferably, the desirable or predetermined catalytic activity index is a CAI of at least 0.8, more preferably a catalytic activity index of at least 0.9.

This invention particularly pertains to exposing activated molecular sieve to gas (i.e., exposing to a gas) environment that contains water. In one embodiment, the gas contacting the sieve (i.e., the gas environment of the sieve) has a relative water pressure of at least 0.0001. In another embodiment, the gas containing water has a relative water pressure of at least 0.001; in another, a relative water pressure of at least 0.01, and in yet another a relative water pressure of at least 0.1.

In one embodiment of the invention, the activated molecular sieve is contacted with a gas containing water, or maintained in an environment having water, which is at a temperature equal to or greater than water critical temperature to minimize water adsorption. In another embodiment, gas containing water can be contacted with activated catalyst below water critical temperature; for example, at a temperature of from about 150° C. to about 300° C., at a temperature of from about 160° C. to about 280° C., and at a temperature of from about 180° C. to about 260° C.

In another embodiment, the activated molecular sieve is contacted with gas containing water or exposed to the environment containing water for a time that does not significantly impact the catalytic activity index. Generally, the activated molecular sieve is contacted with the gas for not greater than about 500 hours, preferably not greater than about 250 hours, more preferably not greater than about 100 hours. In other embodiments, the gas is contacted with the activated molecular sieve from about 0.01 hour to about 50 hours, or from about 0.1 hour to about 50 hours, and more preferably not greater than about 24 hours or about 12 hours or about 6 hours.

In yet another embodiment of the invention, the activated metalloaluminophosphate molecular sieve is contacted with a gas that contains water, but for a time, and at a temperature, that does not significantly affect ethylene or propylene selectivity. Preferably, the activated metalloaluminophosphate molecular sieve is contacted with the gas for a time effective to maintain an ethylene or propylene selectivity of at least about 25 wt %, more preferably at least about 30 wt %, and most preferably at least about 35 wt %.

In one embodiment of the invention, the activated molecular sieve is contacted with gas containing water or exposed to the environment so as to minimize water adsorption. Desirably, the water partial pressure of the contacting gas or the environment is controlled so that activated molecular sieve adsorbs little to no water. Preferably, the activated molecular sieve exposed to the gas containing water or the environment has a water content of not greater than about 1.25 wt %, based on dry weight of the activated molecular sieve. More preferably, the activated molecular sieve has a water content of not greater than about 1.0 wt %, still more preferably not greater than about 0.8 wt %, and most preferably not greater than about 0.5 wt %, based on total weight of the activated molecular sieve.

The molecular sieves used, herein are preferably metalloaluminophosphate molecular sieves that have a molecular framework that include [$AlO_4$] and [$PO_4$] tetrahedral units, such as metal containing aluminophosphates (AlPO). In one embodiment, the metalloaluminophosphate molecular sieves include [$AlO_4$], [$PO_4$] and [$SiO_4$] tetrahedral units, such as silicoaluminophosphates (SAPO). Preferred metalloaluminophosphate molecular sieves include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, and metal containing molecular sieves thereof.

In one embodiment of the invention, the metalloaluminophosphate molecular sieves contain silicon and aluminum. Desirably, the metalloaluminophosphate molecular sieves contain Si and Al at a Si/Al ratio of not greater than about 0.5, preferably not greater than about 0.3, more preferably not greater than about 0.2, still more preferably not greater than about 0.15, and most preferably not greater than about 0.1. In another embodiment, the metalloaluminophosphate molecular sieves contain Si and Al at a ratio of at least about 0.005, more preferably at least about 0.01, and most preferably at least about 0.02.

In a preferred embodiment, catalytic activity is representative of catalytic activity in reaction processes selected from the group consisting of catalytic cracking, hydrocracking, dewaxing, olefin forming reactions, aromatics forming reactions, paraffin isomerization, olefin isomerization, paraffin hydroisomerization, olefin hydroisomerization, olefin oligomerization, olefin polymerization, reforming, alkylation, and disproportionation of aromatics. Olefin forming reactions are preferred.

In a further embodiment, the invention is directed to a method of protecting catalytic activity of an activated metalloaluminophosphate molecular sieve in olefin forming reactions due to contact with water vapor. The method comprises contacting the activated metalloaluminophosphate molecular sieve with a gas for a time effective to maintain the activated metalloaluminophosphate molecular sieve at a desirable or predetermined catalytic activity index (e.g., at a catalytic activity index of at least 0.7, etc.). Preferably, the activated molecular sieve is also maintained at an ethylene or propylene selectivity of at least 25 wt %. The gas contains water up to saturation conditions, e.g., is at a relative water pressure of from 0.0001 to 1. The catalytic activity index can be maintained under conditions where the gas contacts the activated molecular sieve at a temperature less than water critical temperature.

The invention in another aspect is directed to a process for forming olefin product from oxygenate feed. The process comprises contacting an activated metalloaluminophosphate molecular sieve with a gas containing water at conditions effective to maintain the activated sieve at a desirable or predetermined catalytic activity index (e.g., a catalytic activity index of at least 0.7, etc.), preferably at an ethylene or propylene selectivity of at least 25 wt %. The water-contacted sieve can be contacted with an oxygenate feed to form an olefin product, wherein the olefin product contains greater than 50 weight percent olefin, based on total weight of hydrocarbon produced. The olefin in the olefin product can be converted into a variety of products, including polyolefins.

In another embodiment, the invention includes a process for converting oxygenate to an olefin product, which includes a step of loading an activated metalloaluminophosphate molecular sieve into a reaction system. The activated metalloaluminophosphate molecular sieve loaded into the reaction system is contacted with a gas containing water at conditions effective to maintain the activated sieve at an ethylene or propylene selectivity effective to convert an oxygenate feed to an olefin product, with the olefin product containing greater than 50 weight percent olefin, based on total weight of hydrocarbon produced. The water-contacted sieve can then be contacted with an oxygenate feed to form the olefin product, and the olefin product can then be convert to other products such as polyolefins.

The invention further provides a method of activating metalloaluminophosphate molecular sieve. In the method, a metalloaluminophosphate molecular sieve containing template is provided. The metalloaluminophosphate molecular sieve is calcined in a calcination unit to remove the template. Once calcined, gas is swept through the calcination unit to cool the calcined metalloaluminophosphate molecular sieve, while maintaining the calcined metalloaluminophosphate molecular sieve at a desirable catalytic activity index of at least. The sweep gas contains a measurable amount of water, such as a gas having a relative water pressure of at least 0.0001. The gas is desirably sufficiently cool to cool the calcined molecular sieve, such as at a temperature less than water critical temperature.

The invention also includes a method of starting-up an olefin forming reaction system. The method comprises sweeping gas through the reaction system to heat up the system, with the reaction system containing activated metalloaluminophosphate molecular sieve. Gas is swept through the reaction system while maintaining and the activated metalloaluminophosphate molecular sieve at a desirable or predetermined catalytic activity index. The activated metalloaluminophosphate molecular sieve can be contacted in the heated up system with an oxygenate to form an olefin product.

In another aspect, the invention is directed to a method of shutting-down an olefin forming reaction system. The method includes a step of contacting an activated metalloaluminophosphate molecular sieve in a reaction system with an oxygenate to form an olefin product. Contact of the activated metalloaluminophosphate molecular sieve with the oxygenate is stopped and gas is swept through the reaction system to cool down the system. While the gas is swept through the reaction system, the activated metalloaluminophosphate molecular sieve is maintained at a desirable or predetermined catalytic activity index. The system is preferably maintained above water critical temperature, but can be at a temperature less than water critical temperature.

Also provided by the invention is a method of protecting catalytic activity of an activated metalloaluminophosphate molecular sieve in olefin forming reactions due to contact with water vapor. The method comprises contacting the activated metalloaluminophosphate molecular sieve with a gas containing water to effectively maintain the activated metalloaluminophosphate molecular sieve at a desirable or predetermined catalytic activity index, and the activated metalloaluminophosphate molecular sieve contains Si and Al at a Si/Al ratio of not greater than 0.5. In a preferred embodiment, the activated metalloaluminophosphate molecular sieve contains Si and Al at a Si/Al ratio of not greater than 0.3, more preferably not greater than 0.2, still more preferably not greater than 0.15, and most preferably not greater than 0.1.

BRIEF DESCRIPTION OF THE DRAWING

One embodiment of invention is shown in the attached FIGURE, which shows the effect of water on an activated molecular sieve.

DETAILED DESCRIPTION OF THE INVENTION

I. General Description of Invention

This invention is directed to methods for protecting metalloaluminophosphate molecular sieves, particularly silicoaluminophosphate (SAPO) molecular sieves, from loss of catalytic activity due to contact with water. The methods of this invention are particularly effective, because they provide procedures that enable activated sieve to contact water vapor, within a certain range of time, temperature, and water partial pressure conditions, before the sieve becomes substantially deactivated.

The inventors have now found that adsorption of water molecules by an activated metalloaluminophosphate molecular sieve can be controlled by adjusting the conditions of the partial pressure of water in the gas or environment contacting the molecular sieve, the temperature of contact, and the time of contact. Controlling water adsorption controls the rate of deactivation, since generally the more water adsorbed results in a greater rate of deactivation. If activated molecular sieve does not adsorb any water, then there will be little to no deactivation as a result of having activated molecular sieve exposed to the environment.

According to this invention, deactivation of the molecular sieve is determined by a catalytic activity index (CAI). The CAI provides a measure of catalyst deactivation as a result of catalyst exposure temperature, relative water pressure, and water contact time working in concert to deactivate the catalyst. Thus, for example, although a low relative water pressure generally causes less catalyst deactivation, higher relative water pressures may be mitigated by limiting the contact time or controlling the catalyst exposure temperature. The CAI formula of this invention fully describes allowable combinations of time, temperature and relative water pressure to limit catalyst deactivation to specified values.

The catalytic activity index of this invention is defined as the actual catalytic activity at time of measurement divided by the maximum catalytic activity (before any deactivation occurs). In this regard, the CAI would be 0 for a completely deactivated catalyst, and 1 for a catalyst having maximum catalytic activity.

The catalytic activity index (CAI) is calculated according to the following equation.

$$CAI = \exp(f(T) * f(PP_{water})^n * alpha * t)$$

wherein
 t=time of contact of catalyst with water (hours)
 T=temperature at contact (° C.)
 $PP_{water}$=Partial Pressure of water in contact gas (psia)
 alpha=−0.071
 n=3.5
 $f(T) = \exp(ea(1/(T+273) - 1/(T_o+273)))$
 ea=−5500° K $T_o = 200°$ C.

$f(PP_{water}) = (26.2 * PP_{water}/P_{sat} + 1.14) * 0.175$, for $T \geq 180°$ C. (453° K)

$f(PP_{water}) = ((26.2 + 0.272 * (180 - T)) * PP_{water}/P_{sat} + 1.14) * 0.175$, for 180° C. (453° K) > $T \geq 150°$ C. (433° K)

$P_{sat}$ = Saturation pressure of water at T (psia).

In a preferred embodiment, catalytic activity is representative of catalytic activity in reaction processes selected from the group consisting of catalytic cracking, hydrocracking, dewaxing, olefin forming reactions, aromatics forming reactions, paraffin isomerization, olefin isomerization, paraffin hydroisomerization, olefin hydroisomerization, olefin oligomerization, olefin polymerization, reforming, alkylation, and disproportionation of aromatics. In the case of olefin forming reactions, catalyst lifetime is a desirable measurement of catalytic activity. In this invention, a catalyst is considered completely inactive when methanol conversion on a water-free basis is less than 10%.

In one embodiment of the invention, activated metalloaluminophosphate molecular sieve is contacted with a gas that contains water, but for a time, and at a temperature, that does not significantly deactivate the catalyst. Preferably, the activated molecular sieve is contacted with the gas for a time effective to maintain a catalytic activity index (CAI) of at least 0.7. Much below this level, the catalyst is substantially ineffective, and selectivity to desired end products can also be significantly affected. More preferably, the activated molecular sieve is contacted with the gas for a time effective to maintain a catalytic activity index of at least 0.8, and most preferably a catalytic activity index of at least 0.9.

In another embodiment of the invention, the activated metalloaluminophosphate molecular sieve is activated SAPO molecular sieve, and the activated SAPO is contacted with a gas that contains water, but for a time, and at a temperature, that does not significantly affect ethylene or propylene selectivity. Ethylene or propylene selectivity is the actual selectivity of the catalyst to form ethylene or propylene in the product. Preferably, the activated SAPO molecular sieve is contacted with the gas for a time effective to maintain an ethylene or propylene selectivity of at least about 25 wt %, more preferably at least about 30 wt %, and most preferably at least about 35 wt %.

Adsorption of water by activated molecular sieve occurs in situations where gas contacting the activated molecular sieve or the environment in which the activated sieve is in, contains at least a measurable amount of water, i.e., conditions in which the environment or the contacting gas is not considered completely dry. The amount of water in the gas can be effectively determined according to the relative water pressure of the gas. Relative water pressure ($P_r$) in this invention is defined as actual partial pressure of the water ($PP_{water}$) divided by saturated water pressure ($P_{sat}$) at a given temperature below the critical temperature of water (374° C.). The relative water pressure is a measure of the wetness of the environment in which the activated molecular sieve is contacted with the gas. For example, a $P_r = 1$ means 100% water saturation, and a $P_r = 0$ means that the gas or environment is completely dry.

In this invention relative water pressure can range from very low, i.e., low humidity conditions, to a value of 1, saturated water conditions. For example, at 205° C., if the catalyst is purged with room air (at 23° C. and at 71% relative humidity), this air contains water at a patial pressure of 0.29 psia (71/100 * 0.41 = 0.29, where 0.41 psia is the saturation water pressure at 23° C.). When this air is heated up to 205° C., the relative water pressure becomes 0.29/250 = 0.00116, where 250 psia is the saturation water pressure at 205° C. The relative humidity of the gas at 205° C. is 0.00116*100 = 0.116%. This example illustrates that one can use high humidity room air to do the purging at elevated temperature to provide an environment having a low relative water pressure.

In general, the higher the water pressure, the greater the tendency of the contact with the gas to deactivate the catalyst, given constant catalyst exposure temperature and time of gas contact. Nevertheless, by increasing temperature or lowering time of contact, increased water pressure can be tolerated. In one embodiment of the invention, the gas contacting the sieve (i.e., the gas environment of the sieve) has a relative water pressure of at least 0.0001. In another embodiment, the gas containing water has a relative water pressure of at least 0.001; in another, a relative water pressure of at least 0.01, and in yet another a relative water pressure of at least 0.1.

The gas that contains the water and contacts the activated molecular sieve can be any gas that can contain water. Preferably the gas containing the water is selected from the group consisting of air, nitrogen, helium, flue gas, $CO_2$, and any combination thereof. Air is most preferred, as air is generally used in various unit operations such as starting-up and shutting-down the reaction system, including the reactor and regenerator sections of the reaction system.

According to this invention, activated molecular sieve is highly susceptible to water damage at temperatures less than water critical temperature. As generally understood, critical temperature is the temperature above which a gas cannot be liquefied, regardless of the pressure.

In one embodiment of the invention, the activated molecular sieve is contacted with a gas containing water, or maintained in an environment having water, which is at a temperature equal to or greater than water critical temperature to minimize water adsorption. There is no upper limit to the temperature, except to a practical extent of unit operations. For example, a practical temperature limit is generally one not greater than about 1,000° C., preferably not greater than about 900° C., more preferably not greater than about 800° C. In another embodiment, gas containing water can be contacted with activated catalyst below water critical temperature, but at a time and relative water pressure to maintain the desired catalytic activity index. In a particular, embodiment, the gas contacts the activated molecular sieve at a temperature of from about 150° C. to about 300° C. In another embodiment, the gas contacts the activated molecular sieve at a temperature of from about 160° C. to about 280° C., and in yet another embodiment at a temperature of from about 180° C. to about 260° C.

The higher the relative water pressure of the contacting gas, or the lower the temperature of the gas, the greater the effect of loss on catalytic activity. Generally, the activated molecular sieve is contacted with the gas for not greater than about 500 hours. Preferably, the activated molecular sieve is contacted with the gas for not greater than about 250 hours, more preferably not greater than about 100 hours. In other embodiments, the gas is contacted with the activated molecular sieve from about 0.01 hour to about 50 hours, or from about 0.1 hour to about 50 hours, and more preferably not greater than about 24 hours or about 12 hours or about 6 hours.

II. Making and Storing Activated Sieve and Formulated Catalyst

This invention is effective in protecting molecular sieves, such as metalloaluminophosphate molecular sieves, which contain active catalytic sites that are catalytically sensitive to water molecules. Such molecular sieves can be catalytically deactivated as a result of having the active catalytic sites come into significant contact with water molecules.

Even slight amounts of water entrained in the internal pore system of various metalloaluminophosphate molecular sieves can have an undesirable effect on catalytic activity. Desirably, no water should be retained by the activated molecular sieves. Preferably, the activated molecular sieves have a water content of not greater than about 1.25 wt %, based on dry weight of the activated molecular sieve. More preferably, the activated molecular sieve has a water content of not greater than about 1.0 wt %, still more preferably not greater than about 0.8 wt %, and most preferably not greater than about 0.5 wt %, based on total weight of the activated molecular sieve. The amount of water entrained in the activated molecular sieve can be effectively reduced using conventional drying techniques. Preferably, the activated molecular sieve is dried by heating to a temperature of greater than water critical temperature.

Deactivation can occur upon activation of the sieves in an unformulated or formulated state. According to this invention, however, deactivation can be controlled to acceptable limits by controlling one or more variables of time of contact with the water molecules, catalyst temperature at contact, and relative water pressure of the contact environment or any gas contacting the activated sieve.

Contact of activated molecular sieve with water vapor can occur in a variety of process systems and throughout various locations within such process systems. Such processes include the manufacture of the activated molecular sieves or formulated molecular sieve catalysts that have been activated; handling, shipment, and storage of the activated sieves or formulated catalysts; and use of the sieves or catalysts in reactor systems including the reactor and regenerator units in the reactor systems and in catalyst loading, transfer and discharging equipment.

A. Types of Molecular Sieves

The molecular sieves used herein are preferably metalloaluminophosphate molecular sieves that have a molecular framework that include [AlO4] and [PO4] tetrahedral units, such as metal containing aluminophosphates (AlPO). In one embodiment, the metalloaluminophosphate molecular sieves include [AlO4], [PO4] and [SiO4] tetrahedral units, such as silicoaluminophosphates (SAPO). These silicon, aluminum, and phosphorus based molecular sieves and metal-containing derivatives thereof have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO4), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO2]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in R. Szostak, Handbook of Molecular Sieves, Van Nostrand Reinhold, New York, N.Y. (1992), which is herein fully incorporated by reference.

The more preferred molecular sieves are SAPO molecular sieves, and metal-substituted SAPO molecular sieves. Suitable metal substituents are alkali metals of Group IA of the Periodic Table of Elements, an alkaline earth metals of Group IIA of the Periodic Table of Elements, a rare earth metals of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, transition metals of Groups IVB, VB, VIB, VIIB, VIIIB, and IB of the Periodic Table of Elements and mixtures of any of these metal species. In one embodiment, the metal is selected from the group consisting of Co, Cr, Cu, Fe, Ga, Ge, Mg, Mn, Ni, Sn, Ti, Zn and Zr, and mixtures thereof. The metal atoms may be inserted into the framework of a molecular sieve through a tetrahedral unit, such as [MeO2], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the metalloaluminophosphate molecular sieve is represented, on an anhydrous basis, by the formula:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from the group consisting of Group IA, IIA, IB, IIIB, IVB, VB, VIB, VIIB, VIIIB and Lanthanide's of the Periodic Table of Elements. Preferably M is one or more metals selected from the group consisting of Si, Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

In one embodiment of the invention, the metalloaluminophosphate molecular sieves contain silicon and aluminum. In general, lower Si/Al ratios, lead to lower deactivation rates and higher ACIs for a given set of conditions. However, higher Si/Al ratios can be used under the appropriate conditions of temperature, water partial pressure and time of contact with water. Desirably, the metalloaluminophosphate molecular sieves of this invention contain Si and Al, at a Si/Al ratio of not greater than about 0.5, preferably not greater than about 0.3, more preferably not greater than about 0.2, still more preferably not greater than about 0.15, and most preferably not greater than about 0.1. In another embodiment, the Si/Al ratio is sufficiently high to allow for increased catalytic activity of the molecular sieve. Preferably, the metalloaluminophosphate molecular sieves contain Si and Al at a ratio of at least about 0.005, more preferably at least about 0.01, and most preferably at least about 0.02.

Non-limiting examples of SAPO and AlPO molecular sieves useful herein include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO- 11, AlPO- 18, AlPO-31, AlPO-34, AlPO-36, AlPO-37, AlPO-46, and metal containing molecular sieves thereof. Of these, particularly useful molecular sieves are one or a combination of SAPO-18, SAPO-34, SAPO-35, SAPO-44, SAPO-56, AlPO- 18, AlPO-34 and metal containing derivatives thereof, such as one or a combination of SAPO-18, SAPO-34, AlPO-34, AlPO-18, and metal containing derivatives thereof, and especially one or a combination of SAPO-34, AlPO-18, and metal containing derivatives thereof.

In an embodiment, the molecular sieve is an intergrowth material having two or more distinct crystalline phases within one molecular sieve composition. In particular, intergrowth molecular sieves are described in U.S. patent application Publication No. 2002-0165089 and International Publication No. WO 98/15496, published Apr. 16, 1998, both of which are herein fully incorporated by reference. For example, SAPO-18, AlPO-18 and RUW-18 have an AEI framework-type, and SAPO-34 has a CHA framework-type. Thus, the molecular sieve used herein may comprise at least one intergrowth phase of AEI and CHA framework-types, especially where the ratio of CHA framework-type to AEI framework-type, as determined by the DIFFaX method disclosed in U.S. patent application Publication No. 2002-0165089, is greater than 1:1.

Generally, molecular sieves (i.e., molecular sieve crystals) are synthesized by the hydrothermal crystallization of one or more of a source of aluminum, a source of phosphorus, a source of silicon, water and a templating agent, such as a nitrogen containing organic compound. Typically, a combination of sources of silicon and aluminum, or silicon, aluminum and phosphorus, water and one or more templating agents, is placed in a sealed pressure vessel. The vessel is optionally lined with an inert plastic such as polytetrafluoroethylene, and heated under a crystallization pressure and temperature, until a crystalline material is formed, which can then be recovered by filtration, centrifugation and/or decanting.

Non-limiting examples of silicon sources include silicates, fumed silica, for example, Aerosil-200 available from Degussa Inc., New York, N.Y., and CAB-O-SIL M-5, organosilicon compounds such as tetraalkylorthosilicates, for example, tetramethylorthosilicate (TMOS) and tetraethylorthosilicate (TEOS), colloidal silicas or aqueous suspensions thereof, for example Ludox-HS-40 sol available from E.I. du Pont de Nemours, Wilmington, Del., silicic acid or any combination thereof.

Non-limiting examples of aluminum sources include aluminum alkoxides, for example aluminum isopropoxide, aluminum phosphate, aluminum hydroxide, sodium aluminate, pseudo-boehmite, gibbsite and aluminum trichloride, or any combination thereof. A convenient source of aluminum is pseudo-boehmite, particularly when producing a silicoaluminophosphate molecular sieve.

Non-limiting examples of phosphorus sources, which may also include aluminum-containing phosphorus compositions, include phosphoric acid, organic phosphates such as triethyl phosphate, and crystalline or amorphous aluminophosphates such as $AlPO_4$, phosphorus salts, or combinations thereof. A convenient source of phosphorus is phosphoric acid, particularly when producing a silicoaluminophosphate.

In general, templating agents or templates include compounds that contain elements of Group 15 of the Periodic Table of Elements, particularly nitrogen, phosphorus, arsenic and antimony. Typical templates also contain at least one alkyl or aryl group, such as an alkyl or aryl group having from 1 to 10 carbon atoms, for example from 1 to 8 carbon atoms. Preferred templates are nitrogen-containing compounds, such as amines, quaternary ammonium compounds and combinations thereof. Suitable quaternary ammonium compounds are represented by the general formula $R_4N^+$, where each R is hydrogen or a hydrocarbyl or substituted hydrocarbyl group, preferably an alkyl group or an aryl group having from 1 to 10 carbon atoms.

Non-limiting examples of templates include tetraalkyl ammonium compounds including salts thereof, such as tetramethyl ammonium compounds, tetraethyl ammonium compounds, tetrapropyl ammonium compounds, and tetrabutylammonium compounds, cyclohexylamine, morpholine, di-n-propylamine (DPA), tripropylamine, triethylamine (TEA), triethanolamine, piperidine, cyclohexylamine, 2-methylpyridine, N,N-dimethylbenzylamine, N,N-diethylethanolamine, dicyclohexylamine, N,N-dimethylethanolamine, choline, N,N'-dimethylpiperazine, 1,4-diazabicyclo(2,2,2)octane, N',N',N,N-tetramethyl-(1,6)hexanediamine, N-methyldiethanolamine, N-methyl-ethanolamine, N-methyl piperidine, 3-methyl-piperidine, N-methylcyclohexylamine, 3-methylpyridine, 4-methyl-pyridine, quinuclidine, N,N'-dimethyl-1,4-diazabicyclo(2,2,2)octane ion; di-n-butylamine, neopentylamine, di-n-pentylamine, isopropylamine, t-butylamine, ethylenediamine, pyrrolidine, and 2-imidazolidone. Preferred templates are selected from the group consisting of tetraethyl ammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine, heated degraded forms thereof, and combinations thereof.

The pH of the synthesis mixture containing at a minimum a silicon, aluminum, optionally a phosphorus composition, and a templating agent, is generally in the range of from 2 to 10, such as from 4 to 9, for example from 5 to 8.

Generally, the synthesis mixture described above is sealed in a vessel and heated, preferably under autogenous pressure, to a temperature in the range of from about 80° C. to about 250° C., such as from about 100° C. to about 250° C., for example from about 125° C. to about 225° C., such as from about 150° C. to about 180° C.

In one embodiment, the synthesis of molecular sieve crystalline particles is aided by seeds from another or the same framework type molecular sieve.

The time required to form the crystalline particles is usually dependent on the temperature and can vary from immediately up to several weeks. Typically, the crystallization time is from about 30 minutes to around 2 weeks, such as from about 45 minutes to about 240 hours, for example from about 1 hour to about 120 hours. The hydrothermal crystallization may be carried out with or without agitation or stirring.

One method for crystallization involves subjecting an aqueous reaction mixture containing an excess amount of a templating agent to crystallization under hydrothermal conditions, establishing an equilibrium between molecular sieve formation and dissolution, and then, removing some of the excess templating agent and/or organic base to inhibit dissolution of the molecular sieve. See, for example, U.S. Pat. No. 5,296,208, which is herein fully incorporated by reference.

Other methods for synthesizing molecular sieves or modifying molecular sieves are described in U.S. Pat. No. 5,879,655 (controlling the ratio of the templating agent to phosphorus), U.S. Pat. No. 6,005,155 (use of a modifier without a salt), U.S. Pat. No. 5,475,182 (acid extraction), U.S. Pat. No. 5,962,762 (treatment with transition metal), U.S. Pat. Nos. 5,925,586 and 6,153,552 (phosphorus modified), U.S. Pat. No. 5,925,800 (monolith supported), U.S. Pat. No. 5,932,512 (fluorine treated), U.S. Pat. No. 6,046,373 (electromagnetic wave treated or modified), U.S. Pat. No. 6,051,746 (polynuclear aromatic modifier), U.S. Pat. No. 6,225,254 (heating template), PCT WO 01/36329 published May 25, 2001 (surfactant synthesis), PCT WO 01/25151 published Apr. 12, 2001 (staged acid addition), PCT WO 01/60746 published Aug. 23, 2001 (silicon oil), U.S. patent application Ser. No. 09/929,949 filed Aug. 15, 2001 (cooling molecular sieve), U.S. patent application Ser. No. 09/615,526 filed Jul. 13, 2000 (metal impregnation including copper), U.S. patent application Ser. No. 09/672,469 filed Sep. 28, 2000 (conductive microfilter), and U.S. patent application Ser. No. 09/754,812 filed Jan. 4, 2001 (freeze drying the molecular sieve), which are all herein fully incorporated by reference.

Once the crystalline molecular sieve product is formed, usually in a slurry state, it may be recovered by any standard technique well known in the art, for example, by centrifugation or filtration. The recovered crystalline particle product, normally termed the "wet filter cake", may then be washed, such as with water, and then dried, such as in air, before being formulated into a catalyst composition. Alternatively, the wet filter cake may be formulated into a catalyst composition directly, that is without any drying, or after only partial drying.

B. Making Formulated Molecular Sieve Catalyst

1. Components of Formulated Molecular Sieve Catalyst

Molecular sieve catalyst, which contains molecular sieve crystal product, and typically binder and matrix materials, is also referred to as a formulated catalyst. It is made by mixing together molecular sieve crystals (which includes template) and a liquid, optionally with matrix material and/or binder, to form a slurry. The slurry is then dried (i.e., liquid is removed), without completely removing the template from the molecular sieve. Since this dried molecular sieve catalyst includes template, it has not been activated, and is considered a preformed catalyst. The catalyst in this form is resistant to catalytic loss by contact with moisture or water. However, the preformed catalyst must be activated before use, and this invention provides appropriate methods to protect the activated catalyst from significant deactivation.

The liquid used to form the slurry can be any liquid conventionally used in formulating molecular sieve catalysts. Non-limiting examples of suitable liquids include water, alcohol, ketones, aldehydes, esters, or a combination thereof. Water is a preferred liquid.

Matrix materials are optionally included in the slurry used to make the formulated molecular sieve catalyst of this invention. Such materials are typically effective as thermal sinks assisting in shielding heat from the catalyst composition, for example, during regeneration. They can further act to densify the catalyst composition, increase catalyst strength such as crush strength and attrition resistance, and to control the rate of conversion in a particular process. Non-limiting examples of matrix materials include one or more of: rare earth metals, metal oxides including titania, zirconia, magnesia, thoria, beryllia, quartz, silica or sols, and mixtures thereof; for example, silica-magnesia, silica-zirconia, silica-titania, silica-alumina and silica-alumina-thoria.

In one embodiment, matrix materials are natural clays, such as those from the families of montmorillonite and kaolin. These natural clays include kaolins known as, for example, Dixie, McNamee, Georgia and Florida clays. Non-limiting examples of other matrix materials include: halloysite, kaolinite, dickite, nacrite, or anauxite. Optionally, the matrix material, preferably any of the clays, are calcined, acid treated, and/or chemical treated before being used as a slurry component. Under the optional calcination treatment, the matrix material will still be considered virgin material as long as the material has not been previously used in a catalyst formulation.

In a particular embodiment, the matrix material is a clay or a clay-type composition, preferably a clay or clay-type composition having a low iron or titania content, and most preferably the matrix material is kaolin. Kaolin has been found to form a pumpable, high solid content slurry; it has a low fresh surface area, and it packs together easily due to its platelet structure.

Preferably, the matrix material, particularly clay, and preferably kaolin, has an average particle size of from about 0.05 $\mu$m to about 0.75 $\mu$m; more preferably from about 0.1 $\mu$m to about 0.6 $\mu$m. It is also desirable that the matrix material have a $d_{90}$ particle size distribution of less than about 1.5 $\mu$m, preferably less than about 1 $\mu$m.

Binders are also optionally included in the slurry used to make the formulated molecular sieve catalysts of this invention. Such materials act like glue, binding together the molecular sieve crystals and other materials, to form a formulated catalyst composition. Non-limiting examples of binders include various types of inorganic oxide sols such as hydrated aluminas, silicas, and/or other inorganic oxide sols. In one embodiment of the invention, the binder is an alumina-containing sol, preferably aluminium chlorohydrate. Upon calcining, the inorganic oxide sol, is converted into an inorganic oxide matrix component, which is particularly effective in forming a hardened molecular sieve catalyst composition. For example, an alumina sol will convert to an aluminium oxide matrix following heat treatment.

Aluminium chlorohydrate, a hydroxylated aluminium based sol containing a chloride counter ion, also known as aluminium chlorohydrol, has the general formula

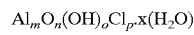

$$Al_mO_n(OH)_oCl_p \cdot x(H_2O)$$

wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105–144, Elsevier, Amsterdam, 1993, which is herein incorporated by reference. In another embodiment, one or more binders are present in combination with one or more other non-limiting examples of alumina materials such as aluminium oxyhydroxide, $\gamma$-alumina, boehmite and transitional aluminas such as $\alpha$-alumina, $\beta$-alumina, $\gamma$-alumina, $\delta$-alumina, $\epsilon$-alumina, κ-alumina, and ρ-alumina, aluminium trihydroxide, such as gibbsite, bayerite, nordstrandite, doyelite, and mixtures thereof.

In another embodiment, the binders are alumina sols, predominantly comprising aluminium oxide, optionally including silicon. In yet another embodiment, the binders are peptised alumina made by treating alumina hydrates such as pseudobohemite, with an acid, preferably a non-halogen acid, to prepare sots or aluminium ion solutions. Non-limiting examples of commercially available colloidal alumina sols include Nalco 8676 available from Nalco Chemical Co., Naperville, Ill., and Nyacol available from the Nyacol Nano Technology Inc., Boston, Mass.

If binder is not used in making the molecular sieve catalyst, the catalyst is considered a binderless catalyst. If binder is used, the amount of binder used to prepare the molecular sieve catalyst ranges from about 2% by weight to about 30% by weight, based on the total weight of the binder, the molecular sieve, and optionally included matrix material, excluding the liquid (i.e., after drying). Preferably the amount of binder used to prepare the molecular sieve catalyst ranges from about 5% by weight to about 20% by weight, more preferably from about 7% by weight to about 15% by weight, based on the total weight of the binder, the molecular sieve, and optionally included matrix material, excluding the liquid (i.e., after drying).

2. Making a Slurry with Molecular Sieve Crystals

The molecular sieve crystals are mixed with liquid, and the optional matrix material and/or binder, using conventional techniques to form a slurry. The components can be mixed in any order, and the mixture is thoroughly stirred to form the slurry. The more thorough the stirring, the better the consistency of the slurry.

The mixing of the slurry is preferably sufficient to break any aggregates or large particles into smaller, more uniform particles. In general, the more vigorous the mixing, the smaller the catalyst particles formed in the slurry. Mixing using high-shear mixers is preferred. In general, high-shear mixers are capable of rotating at speeds of at least about 3,000 rpm laboratory scale equivalent.

Solids particle size of the slurry can be indirectly determined by measuring the viscosity of the slurry. In general, the higher the viscosity, the smaller the solids particle size in the slurry. The viscosity of the slurry should not be too high, so that mixing is not effective in breaking apart large particles, or too low, so that drying will not produce acceptable particle formation.

In one embodiment, the slurry has a viscosity of from about 100 cP (0.1 Pa/sec) to about 9,500 cP (9.5 Pa/sec), as measured using a Brookfield LV-DVE viscometer with a No. 3 spindle at 10 rpm. Preferably, the slurry has a viscosity of from about 200 cP (0.2 Pa/sec) to about 8,500 cP (8.5 Pa/sec), and more preferably from about 350 cP (0.375 Pa/sec) to about 8,000 cP (8 Pa/sec), as measured using a Brookfield LV-DVE viscometer with a No. 3 spindle at 10 rpm.

In another embodiment, the slurry has a solids content of from about 10 wt % to about 75 wt %, based on total weight of the slurry. Preferably the slurry has a solids content of from about 15 wt % to about 70 wt %, more preferably from about 20 wt % to about 65 wt %, based on the total weight of the slurry. The solids content can be measured using any conventional means. However, a CEM MAS 700 microwave muffle furnace is particularly preferred to give results consistent with the values recited herein.

In one embodiment, the slurry used to make the formulated molecular sieve catalyst contains binder and matrix material at a weight ratio of from 0:1 to 1:1. Preferably, the slurry used to make the molecular sieve catalyst contains binder and matrix material at a weight ratio of from 1:15 to 1:2, more preferably 1:10 to 1:2, and most preferably 1:6 to 1:1. In case where binders are not used, the molecular sieve component itself acts as a binder.

3. Making a Preformed Catalyst

Water is removed from the slurry containing the molecular sieve crystals to form a preformed molecular sieve catalyst. Preferably, the slurry is fed to a forming unit that produces the preformed molecular sieve catalyst composition. The forming unit may be any conventional unit, such as a spray dryer, pelletizer, extruder, etc. In a preferred embodiment, the forming unit is spray dryer, which removes water from the slurry by a heating or drying process. Preferably, the forming unit is maintained at a temperature sufficient to remove a majority of the liquid from the slurry.

When a spray dryer is used as the forming (or drying) unit, typically, the slurry of the molecular sieve particles, and optional matrix material and/or binder, is fed to the spray drying unit along with a drying gas. The drying gas contacts the slurry and acts to remove water to form the preformed molecular sieve catalyst. Conventional drying conditions can be used. Such conditions include an average inlet temperature ranging from about 150° C. to about 550° C., and an average outlet temperature ranging from about 100° C. to about 250° C.

During spray drying, the slurry is passed through a nozzle distributing the slurry into small droplets, resembling an aerosol spray, into a drying chamber where atomization occurs. Atomization is achieved by forcing the slurry through a single nozzle or multiple nozzles with a pressure drop in the range of from about 100 psia to about 1,000 psia (about 690 kPaa to about 6,895 kPaa). In another embodiment, the slurry is fed through a single nozzle or multiple nozzles along with an atomization or contacting fluid such as air, steam, flue gas, or any other suitable gas.

In yet another embodiment, the slurry that is used to make the preformed catalyst is directed to the perimeter of a spinning wheel that distributes the slurry into small droplets. The size of the droplets is controlled by one or more factors including slurry viscosity, surface tension, flow rate, pressure, and temperature of the slurry; the shape and dimension of the nozzle(s); or the spinning rate of the wheel. These droplets are then dried in a co-current or counter-current flow of air passing through a spray drier to form a preformed molecular sieve catalyst composition. An example of a conventional spray drying process is described in U.S. Pat. No. 4,946,814, which is incorporated herein by reference.

C. Activating the Sieve or Formulated Catalyst

The molecular sieve material is activated by removing the template from the preformed molecular sieve catalyst composition so as to expose the active catalytic sites to the environment. The template can be removed by any conventional technique, including for example by elution methods or by heating. The molecular sieve crystals themselves can be activated for immediate catalytic use or for storing or transporting prior to use. However, it is preferred that the molecular sieves be formulated into a preformed catalyst, then activated, since the sieves are typically most useful as a formulated product. The formulated product generally provides the most effective particle size and hardness for commercial scale equipment.

In one embodiment of the invention, the molecular sieve material is activated by removing the template by heat. In a preferred embodiment, the heat is sufficient to remove water that is formed as a result of the combustion of the template. Preferably, the molecular sieve material is heated at a temperature greater than the critical temperature of water. At this temperature, water formed during the combustion process will not condense or be retained by the molecular sieve. Preferably, the template is removed by contacting with steam at a temperature greater than the critical temperature of water. More preferably, following removal of the template, any water entrained in the catalyst is also removed, preferably by appropriate heating using a dry gas. Preferably, the dry gas has a relative water pressure of less than 0.0001.

Heating to remove template and activate the molecular sieve is generally referred to in this invention as calcination. Conventional calcination devices can be used. Such devices include rotary calciners, fluid bed calciners, batch ovens, and the like. Calcination time is typically dependent on the degree of hardening of the molecular sieve catalyst composition and the temperature.

Conventional calcination temperatures are effective to remove template materials and to activate the molecular sieve catalyst of this invention. Such temperatures are generally in the range from about 400° C. to about 1,000° C., preferably from about 500° C. to about 800° C., and most preferably from about 550° C. to about 700° C.

D. Storage of Activated Sieve or Formulated Catalyst

Following heat activation by calcining for example, the activated molecular sieve is cooled, since it will generally be at a temperature that is too high for immediately handling or loading into a container. In a preferred embodiment, the activated molecular sieve or formulated molecular sieve catalyst is cooled and stored so that there is not a substantial reduction in catalytic activity index.

In one embodiment, molecular sieve containing template or a preformed catalyst is calcined in a calcination unit to activate the molecular sieve. Following calcination, the activated molecular sieve or catalyst containing the activated molecular sieve (collectively activated molecular sieve) is cooled, and placed in a container for transport or storage. This activation and subsequent cooling can be carried out in separate units or in the same unit, particularly in separate regions of the same unit.

Once the temperature of the catalyst falls below water critical temperature, catalyst deactivation begins to occur as water molecules will generally be present as a result of the combustion process. Gas can be swept through the calcination unit to aid in cooling, and the sweep gas can also contain water vapor. Although the presence of water molecules can deactivate active catalytic sites, the presence of some water is tolerated according to this invention, since catalyst temperature and time of contact with water vapor can be controlled to minimize catalyst deactivation.

Examples of sweep gas (the gas contacting the activated molecular sieve) include air, nitrogen, helium, flue gas, $CO_2$, and any combination thereof. The gas that contacts the activated molecular sieve contains at least a measurable amount of water, typically having a relative water pressure of at least 0.0001. By increasing temperature or lowering time of contact, increased water pressure can be tolerated. In one embodiment, the gas containing water has a relative water pressure of at least 0.001; in another, a relative water pressure of at least 0.01, and in yet another a relative water pressure of at least 0.1.

At temperatures where water adsorption by the activated catalyst can occur (e.g., below water critical temperature, such as not greater than 300° C., 280° C. or 260° C.), the activated molecular sieve is contacted with the sweep gas (i.e., the gas is swept through the calcination unit) to cool the molecular sieve, and for a time effective to maintain a catalytic activity index of at least 0.7, preferably at least 0.8, and more preferably at least 0.9. The activated molecular sieve is desirably contacted with the sweep gas (i.e., the gas is swept through the calcination unit) for not greater than 500 hours, preferably not greater than 250 hours, more preferably not greater than 100 hours. In other embodiments, the sweep gas is contacted with the activated molecular sieve in the calcination unit from 0.01 hour to 50 hours, or from 0.1 hour to 50 hours, and more preferably not greater than 24 hours or 12 hours or about 6 hours.

In yet another embodiment of the invention, the container provides an anhydrous environment for the activated sieve. Such an environment can be provided by covering the activated sieve loaded into a container with a gas or liquid blanket under anhydrous conditions. As provided herein, the anhydrous gas or liquid blanket will have no more than a limited amount of water. The anhydrous gas blanket can be provided under vacuum conditions or under atmospheric or greater pressure conditions, and will desirably have not greater than about 1.2 volume percent water, preferably not greater than about 0.2 volume percent water, and more preferably not greater than about 0.02 volume percent water. The anhydrous liquid blanket will desirably have not greater than about 200 ppm water, preferably not greater than about 100 ppm water, and more preferably not greater than about 50 ppm water. The anhydrous environment can be applied during storage, transport or loading of the activated material.

The anhydrous gas blanket is a gas under standard temperature and pressure conditions and does not react to any significant degree with the molecular sieve structure. The gas is preferably selected from the group consisting of nitrogen, helium, CO, $CO_2$, $H_2$, argon, $O_2$, light alkanes (especially $C_1$–$C_4$ alkanes, particularly methane and ethane), cyclo-alkanes and mixtures thereof, e.g. air. Air is a preferred gas. The gas blanket can be maintained at any pressure, including under vacuum or at pressures above standard, even if the gas becomes liquid at pressures above standard, as long as the conditions remain anhydrous.

The anhydrous liquid blanket is a liquid under standard temperature and pressure conditions, and does not react to any significant degree with the molecular sieve structure. The liquid is preferably selected from the group consisting of alkanes, cyclo-alkanes, $C_6$–$C_{30}$ aromatics, alcohols, particularly $C_4$+ branched alcohols.

III. Reaction System Operations in the Presence of Water

The methods of this invention can be used in any reaction systems that use metalloaluminophosphate molecular sieves containing active catalytic sites that are catalytically sensitive to water molecules. Such reaction systems include catalytic cracking, hydrocracking, dewaxing, olefin forming reactions, aromatics forming reactions, paraffin isomerization, olefin isomerization, paraffin hydroisomerization, olefin hydroisomerization, olefin oligomerization, olefin polymerization, reforming, alkylation, and disproportionation of aromatics.

In operation, the various reaction systems are generally operated at temperatures above the water critical temperature. In certain unit operations, e.g., unit start-up, unit shut-down, unit interruptions, etc., temperatures may drop to below water critical temperature. If water vapor is present when temperatures drop to below the water critical temperature, catalyst deactivation occurs. It is, therefore, important that the reaction systems be operated to control one or more variables of time of contact with the water molecules, temperature drop below the critical water temperature, and relative water pressure in the reaction system.

In one embodiment, the reaction system is heated to start-up the reaction system by sweeping a gas containing water through at least a part of the system. Examples of sweep gas (the gas contacting the activated molecular sieve) include air, nitrogen, helium, flue gas, $CO_2$, and any combination thereof. The gas that contacts the activated molecular sieve contains at least a measurable amount of water, typically having a relative water pressure of at least 0.0001. By increasing temperature or lowering time of contact, increased water pressure can be tolerated. Increased water pressure is also desired to the extent that water generally has a higher heat capacity than dry gas, so the water will have a greater effect on heating up the reaction system. In one embodiment, the gas containing water has a relative water pressure of at least 0.001; in another, a relative water pressure of at least 0.01, and in yet another a relative water pressure of at least 0.1.

The gas that is used to sweep the reaction system at start-up is desirably above water critical temperature. However, at initial start-up procedures the environment will likely be cooler than the gas itself. In such an environment, it is desirable to maintain a temperature of at least about 150° C. where there is contact with water molecules in the sweep gas and the activated catalyst. At system temperatures below water critical temperature, e.g., not greater than 300° C., 280° C. or 260° C., the activated molecular sieve is contacted with the sweep gas (i.e., the gas is swept through the system) for a time effective to maintain a catalytic activity index of at least 0.7, preferably at least 0.8, and more preferably at least 0.9. The activated molecular sieve is loaded into the system either before or during the start-up procedure, and is desirably contacted with the sweep gas (i.e., the gas is swept through the system) for not greater than 500 hours, preferably not greater than 250 hours, more preferably not greater than 100 hours. In other embodiments, the sweep gas is contacted with the activated molecular sieve from 0.01 hour to 50 hours, or from 0.1 hour to 50 hours, and more preferably not greater than 24 hours or 12 hours or about 6 hours.

It is desirable to heat up the reaction system as quickly as possible so as to minimize any possible damage to the catalyst in the system as a result of the catalyst coming into contact with moisture below the critical water temperature. Once, the system is above critical water temperature, and is at a desirable start-up temperature, circulation of the sweep gas is stopped and feed introduced. The feed is then contacted with the activated catalyst in the system to form desirable product. In a preferred embodiment, the feed is an oxygenate and the product is an olefin-containing product.

In one embodiment, the reaction system is cooled to shut-down the reaction. At shut-down gas is also swept through the system to cool the system down. Water molecules will generally be present in the gas during this unit operation. Examples of sweep gas (the gas contacting the activated molecular sieve) include air, nitrogen, helium, flue gas, $CO_2$, and any combination thereof. The gas that contacts the activated molecular sieve contains at least a measurable amount of water, typically having a relative water pressure of at least 0.0001. By increasing temperature or lowering time of contact, increased water pressure can be tolerated. Increased water pressure is also desired to the extent that water generally has a higher heat capacity than dry gas, so the water will have a greater effect on cooling down the reaction system. In one embodiment, the gas containing water has a relative water pressure of at least 0.001; in another, a relative water pressure of at least 0.01, and in yet another a relative water pressure of at least 0.1.

The gas that is used to sweep the reaction system at shut-down will eventually fall below water critical temperature. It is desirable to maintain a shut-down temperature of at least about 150° C. for as long as reasonable where there is contact with water molecules in the sweep gas and the activated catalyst. At temperatures below water critical temperature, e.g., not greater than 300° C., 280° C. or 260° C., the activated molecular sieve is contacted with the sweep gas (i.e., the gas is swept through the system) for a time effective to maintain a catalytic activity index of at least 0.7, preferably at least 0.8, and more preferably at least 0.9. The activated molecular sieve is desirably contacted with the sweep gas (i.e., the gas is swept through the system) for not greater than 500 hours, preferably not greater than 250 hours, more preferably not greater than 100 hours. In other embodiments, the sweep gas is contacted with the activated molecular sieve from 0.01 hour to 50 hours, or from 0.1 hour to 50 hours, and more preferably not greater than 24 hours or 12 hours or about 6 hours.

During unit interruptions, it is desirable to maintain the reaction system at temperatures at least as high as water critical temperature. However, heat maintenance during unit interruptions can be difficult, leading to cool-down conditions. Under conditions where the temperature drops to lower than water critical temperature, the reaction system can be effectively operated as in shut-down mode.

In one embodiment of the invention, the reaction system is an olefin forming reaction system in which feedstock is converted into one or more olefin(s). Typically, the feedstock contains one or more aliphatic-containing compounds such that the aliphatic moiety contains from 1 to about 50 carbon atoms, such as from 1 to 20 carbon atoms, for example from 1 to 10 carbon atoms, and particularly from 1 to 4 carbon atoms.

Non-limiting examples of aliphatic-containing compounds include alcohols such as methanol and ethanol, alkyl mercaptans such as methyl mercaptan and ethyl mercaptan, alkyl sulfides such as methyl sulfide, alkylamines such as methylamine, alkyl ethers such as dimethyl ether, diethyl ether and methylethyl ether, alkyl halides such as methyl chloride and ethyl chloride, alkyl ketones such as dimethyl ketone, formaldehydes, and various acids such as acetic acid.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) produced from the feedstock typically have from 2 to 30 carbon atoms, preferably 2 to 8 carbon atoms, more preferably 2 to 6 carbon atoms, still more preferably 2 to 4 carbons atoms, and most preferably are ethylene and/or propylene.

The catalyst composition of the invention is particularly useful in the process that is generally referred to as the gas-to-olefins (GTO) process or, alternatively, the methanol-to-olefins (MTO) process. In this process, an oxygenated feedstock, most preferably a methanol-containing feedstock, is converted in the presence of a molecular sieve catalyst composition into one or more olefin(s), preferably and predominantly, ethylene and/or propylene.

Using the catalyst composition of the invention for the conversion of a feedstock, preferably a feedstock containing one or more oxygenates, the amount of olefin(s) produced based on the total weight of hydrocarbon produced is greater than 50 weight percent, typically greater than 60 weight percent, such as greater than 70 weight percent, and preferably greater than 75 weight percent. In one embodiment, the amount of ethylene and/or propylene produced based on the total weight of hydrocarbon product produced is greater than 65 weight percent, such as greater than 70 weight percent, for example greater than 75 weight percent, and preferably greater than 78 weight percent. Typically, the amount ethylene produced in weight percent based on the total weight of hydrocarbon product produced, is greater than 30 weight percent, such as greater than 35 weight percent, for example greater than 40 weight percent. In addition, the amount of propylene produced in weight percent based on the total weight of hydrocarbon product produced is greater than 20 weight percent, such as greater than 25 weight percent, for example greater than 30 weight percent, and preferably greater than 35 weight percent.

In addition to the oxygenate component, such as methanol, the feedstock may contains one or more diluent(s), which are generally non-reactive to the feedstock or molecular sieve catalyst composition and are typically used to reduce the concentration of the feedstock. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, for example water, may be used either in a liquid or a vapor form, or a combination thereof. The diluent may be either added directly to the feedstock entering a reactor or added directly to the reactor, or added with the molecular sieve catalyst composition.

The present process can be conducted over a wide range of temperatures, such as in the range of from about 200° C. to about 1000° C., for example-from about 250° C. to about 800° C., including from about 250° C. to about 750° C., conveniently from about 300° C. to about 650° C., typically from about 350° C. to about 600° C. and particularly from about 350° C. to about 550° C.

Similarly, the present process can be conducted over a wide range of pressures including autogenous pressure. Typically the partial pressure of the feedstock exclusive of any diluent therein employed in the process is in the range of from about 0.1 kPaa to about 5 MPaa, such as from about 5 kPaa to about 1 MPaa, and conveniently from about 20 kPaa to about 500 kPaa.

The weight hourly space velocity (WHSV), defined as the total weight of feedstock excluding any diluents per hour per weight of molecular sieve in the catalyst composition, typically ranges from about 1 hr$^{-1}$ to about 5000 hr$^{-1}$, such as from about 2 hr$^{-1}$ to about 3000 hr$^{-1}$, for example from about 5 hr$^{-1}$ to about 1500 hr$^{-1}$, and conveniently from about 10 hr$^{-1}$ to about 1000 hr$^{-1}$. In one embodiment, the WHSV is greater than 20 hr$^{-1}$ and, where feedstock contains methanol and/or dimethyl ether, is in the range of from about 20 hr$^{-1}$ to about 300 hr$^{-1}$.

Where the process is conducted in a fluidized bed, the superficial gas velocity (SGV) of the feedstock including diluent and reaction products within the reactor system, and particularly within a riser reactor(s), is at least 0.1 meter per second (m/sec), such as greater than 0.5 m/sec, such as greater than 1 m/sec, for example greater than 2 m/sec, conveniently greater than 3 m/sec, and typically greater than 4 m/sec. See for example U.S. patent application Ser. No. 09/708,753 filed Nov. 8, 2000, which is herein incorporated by reference.

The process of the invention is conveniently conducted as a fixed bed process, or more typically as a fluidized bed process (including a turbulent bed process), such as a continuous fluidized bed process, and particularly a continuous high velocity fluidized bed process.

The process can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. Nos. 4,076,796, 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor types are riser reactors generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In one practical embodiment, the process is conducted as a fluidized bed process or high velocity fluidized bed process utilizing a reactor system, a regeneration system and a recovery system.

In such a process the reactor system conveniently includes a fluid bed reactor system having a first reaction zone within one or more riser reactor(s) and a second reaction zone within at least one disengaging vessel, typically comprising one or more cyclones. In one embodiment, the one or more riser reactor(s) and disengaging vessel are contained within a single reactor vessel. Fresh feedstock, preferably containing one or more oxygenates, optionally with one or more diluent(s), is fed to the one or more riser reactor(s) into which a molecular sieve catalyst composition or coked version thereof is introduced. In one embodiment, prior to being introduced to the riser reactor(s), the molecular sieve catalyst composition or coked version thereof is contacted with a liquid, preferably water or methanol, and/or a gas, for example, an inert gas such as nitrogen.

In an embodiment, the amount of fresh feedstock fed as a liquid and/or a vapor to the reactor system is in the range of from 0.1 weight percent to about 85 weight percent, such as from about 1 weight percent to about 75 weight percent, more typically from about 5 weight percent to about 65 weight percent based on the total weight of the feedstock including any diluent contained therein. The liquid and vapor feedstocks may be the same composition, or may contain varying proportions of the same or different feedstocks with the same or different diluents.

The feedstock entering the reactor system is preferably converted, partially or fully, in the first reactor zone into a gaseous effluent that enters the disengaging vessel along with the coked catalyst composition. In the preferred embodiment, cyclone(s) are provided within the disengaging vessel to separate the coked catalyst composition from the gaseous effluent containing one or more olefin(s) within the disengaging vessel. Although cyclones are preferred, gravity effects within the disengaging vessel can also be used to separate the catalyst composition from the gaseous effluent. Other methods for separating the catalyst composition from the gaseous effluent include the use of plates, caps, elbows, and the like.

In one embodiment, the disengaging vessel includes a stripping zone, typically in a lower portion of the disengaging vessel. In the stripping zone the coked catalyst composition is contacted with a gas, preferably one or a combination of steam, methane, carbon dioxide, carbon monoxide, hydrogen, or an inert gas such as argon, preferably steam, to recover adsorbed hydrocarbons from the coked catalyst composition that is then introduced to the regeneration system.

The coked catalyst composition is withdrawn from the disengaging vessel and introduced to the regeneration system. The regeneration system comprises a regenerator where the coked catalyst composition is contacted with a regeneration medium, preferably a gas containing oxygen, under conventional regeneration conditions of temperature, pressure and residence time.

Non-limiting examples of suitable regeneration media include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. Suitable regeneration conditions are those capable of burning coke from the coked catalyst composition, preferably to a level less than 0.5 weight percent based on the total weight of the coked molecular sieve catalyst composition entering the regeneration system. For example, the regeneration temperature may be in the range of from about 200° C. to about 1500° C., such as from about 300° C. to about 1000° C., for example from about 450° C. to about 750° C., and conveniently from about 550° C. to 700° C. The regeneration pressure may be in the range of from about 15 psia (103 kPaa) to about 500 psia (3448 kPaa), such as from about 20 psia (138 kPaa) to about 250 psia (1724 kPaa), including from about 25 psia (172kPaa) to about 150 psia (1034 kPaa), and conveniently from about 30 psia (207 kPaa) to about 60 psia (414 kPaa).

The residence time of the catalyst composition in the regenerator may be in the range of from about one minute to several hours, such as from about one minute to 100 minutes, and the volume of oxygen in the regeneration gas may be in the range of from about 0.01 mole percent to about 5 mole percent based on the total volume of the gas.

The burning of coke in the regeneration step is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated catalyst composition from the regeneration system and passing it through a catalyst cooler to form a cooled regenerated catalyst composition. The catalyst cooler, in an embodiment, is a heat exchanger that is located either internal or external to the regeneration system. Other methods for operating a regeneration system are in disclosed U.S. Pat. No. 6,290,916 (controlling moisture), which is herein fully incorporated by reference.

The regenerated catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In one embodiment, the regenerated catalyst composition withdrawn from the regeneration system is returned to the riser reactor(s) directly, preferably after passing through a catalyst cooler. A carrier, such as an inert gas, feedstock vapor, steam or the like, may be used, semi-continuously or continuously, to facilitate the introduction of the regenerated catalyst composition to the reactor system, preferably to the one or more riser reactor(s).

By controlling the flow of the regenerated catalyst composition or cooled regenerated catalyst composition from the regeneration system to the reactor system, the optimum level of coke on the molecular sieve catalyst composition entering the reactor is maintained. There are many techniques for controlling the flow of a catalyst composition described in Michael Louge, *Experimental Techniques, Circulating Fluidized Beds*, Grace, Avidan and Knowlton, eds., Blackie, 1997 (336–337), which is herein incorporated by reference.

Coke levels on the catalyst composition are measured by withdrawing the catalyst composition from the conversion process and determining its carbon content. Typical levels of coke on the molecular sieve catalyst composition, after regeneration, are in the range of from 0.01 weight percent to about 15 weight percent, such as from about 0.1 weight percent to about 10 weight percent, for example from about 0.2 weight percent to about 5 weight percent, and conveniently from about 0.3 weight percent to about 2 weight percent based on the weight of the molecular sieve.

The gaseous effluent is withdrawn from the disengaging system and is passed through a recovery system. There are many well known recovery systems, techniques and sequences that are useful in separating olefin(s) and purifying olefin(s) from the gaseous effluent. Recovery systems generally comprise one or more or a combination of various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment, for example various condensers, heat exchangers, refrigeration systems or chill trains, compressors, knock-out drums or pots, pumps, and the like.

Non-limiting examples of these towers, columns, splitters or trains used alone or in combination include one or more of a demethanizer, preferably a high temperature demethanizer, a dethanizer, a depropanizer, a wash tower often referred to as a caustic wash tower and/or quench tower, absorbers, adsorbers, membranes, ethylene (C2) splitter, propylene (C3) splitter and butene (C4) splitter.

Various recovery systems useful for recovering olefin(s), such as ethylene, propylene and/or butene, are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Other recovery systems that include purification systems, for example for the purification of olefin(s), are described in *Kirk-Othmer Encyclopedia of Chemical Technology*, 4th Edition, Volume 9, John Wiley & Sons, 1996, pages 249–271 and 894–899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which are herein incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Typically, in converting one or more oxygenates to olefin(s) having 2 or 3 carbon atoms, a minor amount hydrocarbons, particularly olefin(s), having 4 or more carbon atoms is also produced. The amount of $C_4+$ hydrocarbons is normally less than 20 weight percent, such as less than 10 weight percent, for example less than 5 weight percent, and particularly less than 2 weight percent, based on the total weight of the effluent gas withdrawn from the process, excluding water. Typically, therefore the recovery system may include one or more reaction systems for converting the $C_4+$ impurities to useful products.

Non-limiting examples of such reaction systems are described in U.S. Pat. No. 5,955,640 (converting a four carbon product into butene-1), U.S. Pat. No. 4,774,375 (isobutane and butene-2 oligomerized to an alkylate gasoline), U.S. Pat. No. 6,049,017 (dimerization of n-butylene), U.S. Pat. Nos. 4,287,369 and 5,763,678 (carbonylation or hydroformulation of higher olefins with carbon dioxide and hydrogen making carbonyl compounds), U.S. Pat. No. 4,542,252 (multistage adiabatic process), U.S. Pat. No. 5,634,354 (olefin-hydrogen recovery), and Cosyns, J. et al., *Process for Upgrading C3, C4 and C5 Olefinic Streams*, Pet. & Coal, Vol. 37, No. 4 (1995) (dimerizing or oligomerizing propylene, butylene and pentylene), which are all fully herein incorporated by reference.

The preferred light olefin(s) produced by any one of the processes described above are high purity prime olefin(s) products that contain a single carbon number olefin in an amount greater than 80 percent, such as greater than 90 weight percent, such as greater than 95 weight percent, for example at least about 99 weight percent, based on the total weight of the olefin.

In one practical embodiment, the process of the invention forms part of an integrated process for producing light olefin(s) from a hydrocarbon feedstock, preferably a gaseous hydrocarbon feedstock, particularly methane and/or ethane. The first step in the process is passing the gaseous feedstock, preferably in combination with a water stream, to a syngas production zone to produce a synthesis gas (syngas) stream, typically comprising carbon dioxide, carbon monoxide and hydrogen. Syngas production is well known, and typical syngas temperatures are in the range of from about 700° C. to about 1200° C. and syngas pressures are in the range of from about 2 MPa to about 100 MPa. Synthesis gas streams are produced from natural gas, petroleum liquids, and carbonaceous materials such as coal, recycled plastic, municipal waste or any other organic material. Preferably synthesis gas stream is produced via steam reforming of natural gas.

The next step in the process involves contacting the synthesis gas stream generally with a heterogeneous catalyst, typically a copper based catalyst, to produce an oxygenate containing stream, often in combination with water. In one embodiment, the contacting step is conducted at temperature in the range of from about 150° C. to about 450° C. and a pressure in the range of from about 5 MPa to about 10 MPa.

This oxygenate containing stream, or crude methanol, typically contains the alcohol product and various other components such as ethers, particularly dimethyl ether, ketones, aldehydes, dissolved gases such as hydrogen methane, carbon oxide and nitrogen, and fuel oil. The oxygenate containing stream, crude methanol, in the preferred embodiment is passed through a well known purification processes, distillation, separation and fractionation, resulting in a purified oxygenate containing stream, for example, commercial Grade A and AA methanol.

The oxygenate containing stream or purified oxygenate containing stream, optionally with one or more diluents, can then be used as a feedstock in a process to produce light olefin(s), such as ethylene and/or propylene. Non-limiting examples of this integrated process are described in EP-B-0 933 345, which is herein fully incorporated by reference.

In another more fully integrated process, that optionally is combined with the integrated processes described above, the olefin(s) produced are directed to, in one embodiment, one or more polymerization processes for producing various polyolefins. (See for example U.S. patent application Ser. No. 09/615,376 filed Jul. 13, 2000, which is herein fully incorporated by reference.)

Polymerization processes include solution, gas phase, slurry phase and a high pressure processes, or a combination thereof. Particularly preferred is a gas phase or a slurry phase polymerization of one or more olefin(s) at least one of which is ethylene or propylene. These polymerization processes utilize a polymerization catalyst that can include any one or a combination of the molecular sieve catalysts discussed above. However, the preferred polymerization catalysts are the Ziegler-Natta, Phillips-type, metallocene, metallocene-type and advanced polymerization catalysts, and mixtures thereof.

In a preferred embodiment, the integrated process comprises a process for polymerizing one or more olefin(s) in the presence of a polymerization catalyst system in a polymerization reactor to produce one or more polymer products, wherein the one or more olefin(s) have been made by converting an alcohol, particularly methanol, using a molecular sieve catalyst composition as described above. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

The polymers produced by the polymerization processes described above include linear low density polyethylene, elastomers, plastomers, high density polyethylene, low density polyethylene, polypropylene and polypropylene copolymers. The propylene based polymers produced by the polymerization processes include atactic polypropylene, isotactic polypropylene, syndiotactic polypropylene, and propylene random, block or impact copolymers.

IV. EXAMPLES

A. Example 1

An activated SAPO-34 molecular sieve catalyst was loaded into a tapered element oscillating microbalance (TEOM, Series 1500 Pulse Mass Analyzer from Rupprecht and Patashnick), and calcined under air at 625° C. until all the coke present on the catalyst was removed. Coke removal was considered complete when the change of mass measured by the TEOM reactor, as a function of time, was approximately zero. The duration of calcination was approximately one hour. After calcination was complete, the reactor temperature was brought to a methanol to olefins (MTO) reaction condition of 425° C., and allowed to stabilize. Subsequently, methanol at a constant flow rate was introduced to the reactor, and the MTO reaction was allowed to proceed. The products of the reaction (i.e., $C_2$–$C_5$ hydrocarbons) were measured at discrete intervals of time using gas chromatography (GC). The mass gain of the catalyst (due to coke formation on the catalyst) as a function of time was recorded by the TEOM analytical unit. The MTO reaction was allowed to proceed until the catalyst had sufficiently deactivated due to coke deposition on the catalyst. Deactivation due to coke was considered complete when methanol conversion on a water-free basis was less than 10%. This procedure was performed in order to determine the catalytic activity of a catalyst that has not been subjected to steam (i.e., maximum catalytic activity).

Once the catalytic activity of the undamaged catalyst (i.e., maximum catalytic activity) was determined, the catalyst was calcined using the same procedure as above. After calcination was complete, the TEOM reactor was brought to various temperatures and partial pressures of steam. The partial pressure of steam was controlled by either introducing pure steam to the reactor and adjusting the total reactor pressure, or by diluting the steam with nitrogen to achieve a desired partial pressure at a constant total reactor pressure. This temperature/partial pressure condition was held for measured durations of time, generally between 4 and 12 hours, depending on the time scale of deactivation. After the steaming portion of the test was complete, nitrogen was flowed through the catalyst sample in order to remove much of the adsorbed water on the catalyst. That is, nitrogen was flowed through the catalyst bed until the mass lost as a function of time was approximately zero. The molecular sieve was then heated to 425° C. and allowed to equilibrate. The MTO reaction was run following the same procedure outlined above. Once the reaction was complete and samples analyzed by GC, the results of the analysis of the steam treated sample were compared to that of the undamaged sample. The catalyst was then calcined and treated with steam using the procedure previously outlined to further damage the catalyst.

This procedure was repeated to determine steam damage as a function of time at a given temperature and partial pressure of steam. Many temperature and partial pressure combinations were tested, starting with an undamaged sample, in order to calculate the effect of temperature and steam partial pressure upon catalyst deactivation.

Once an acceptable matrix of experiments was completed (experiments performed at various temperature/steam partial pressure conditions), relative catalytic activity indices were determined and compared as functions of temperature, steam partial pressure and time of contact with steam. The results are shown in the FIGURE.

In this Example, catalyst deactivation was taken to be the lessening of the catalyst lifetime relative to an undamaged catalyst. Catalyst lifetime was taken to be the amount of time taken for a given catalyst to achieve less than 10% conversion of methanol on a water free basis. Deactivation is therefore presented as a fraction, that fraction being the ratio of the lifetime of the damaged catalyst over the lifetime undamaged catalyst.

Referring to the FIGURE, two different values for CAI are shown, 0.8, and 0.95. All the points on each plane shown have the same CAI value. At any combination of time, temperature, and water partial pressure above a particular plane, the CAI will be less than the listed value. For example, Point 1 of the FIGURE represents catalyst being exposed to gas at a water partial pressure of 30.8 psia at 170° C. for 1.5 hours. The CAI at these conditions is 0.8. By decreasing water partial pressure to 18.7 psia, and keeping temperature and time of contact constant, the CAI is increased to 0.95. See Point 2 of the FIGURE. Thus, the FIGURE demonstrates the effects of water partial pressure, temperature and contact time on catalytic activity of activated metalloaluminophosphate molecular sieve catalyst.

B. Example 2

The data from Example 1 was used to calculate a formula for catalytic activity index (CAI). The formula is as follows:

$$CAI = \exp(f(T) * f(PP_{water})^n * \mathrm{alpha} * t)$$

wherein
t=time of contact of catalyst with water (hours)
T=temperature at contact (° C.)
$PP_{water}$=Partial Pressure of water in contact gas (psia)
alpha=–0.071
n=3.5
$f(T) = \exp(ea(1/(T+273) - 1/(T_o+273)))$
ea=–5500° K $T_o$=200° C.
$f(PP_{water})$=(26.2*$PP_{water}$/$P_{sat}$+1.14)*0.175, for T≧180° C. (453° K)
$f(PP_{water})$=((26.2+0.272*(180−T))*$PP_{water}$/$P_{sat}$+1.14) *0.175, for 180° C. (453° K)>T≧150° C. (433° K)
$P_{sat}$=Saturation pressure of water at T (psia)

Various water partial pressures, time of contact of catalyst with water-containing gas, and contact temperatures were entered into the formula to calculate the corresponding catalytic activity indices. The results are shown in Table 1.

TABLE 1

| $PP_{water}$ | Time | CAI at contact temperature (T) | | |
|---|---|---|---|---|
| (psia) | (t, hours) | 160° C. | 200° C. | 250° C. |
| 15 | 6 | 0.82 | 0.96 | 0.98 |
|  | 12 | 0.67 | 0.92 | 0.95 |
| 25 | 6 | 0.37 | 0.88 | 0.95 |
|  | 12 | 0.14 | 0.77 | 0.9 |
| 40 | 6 | 0.01 | 0.64 | 0.88 |
|  | 12 | 1.50E−04 | 0.4 | 0.77 |

Table 1 shows the effects of water pressure, time of contact of catalyst with water vapor, and temperature of contact on CAI. The lower the CAI, the less active the catalyst. In general, the higher the temperature, the lower the water partial pressure, and the lower the time of contact with water, the higher the CAI, which is highly desirable.

C. Example 3

Several catalysts (all metalloaluminophosphate molecular sieves) with various Si/Al ratio were tested under steaming conditions similar to the ones described in Example 2. Table 2 below describes steaming conditions and resulting CAI under the various Si/Al ratios.

TABLE 2

| Catalyst | Si/Al | PPwater (psia) | T (° C.) | time (t, hours) | CAI |
|---|---|---|---|---|---|
| A | 0.16 | 40 | 180 | 16 | 0.35 |
| B | 0.07 | 40 | 180 | 16 | 0.8 |
| C | 0.02 | 40 | 225 | 16 | 1.0 |

The data in Table 2 demonstrates that lower Si/Al ratios lead to lower deactivation rates and higher CAIs for a given set of conditions.

Having now fully described this invention, it will be appreciated by those skilled in the art that the invention can be performed within a wide range of parameters within what is claimed, without departing from the spirit and scope of the invention.

The invention claimed is:

1. A method of protecting activated metalloaluminophosphate molecular sieve from loss of catalytic activity, comprising contacting the activated metalloaluminophosphate molecular sieve with a gas containing water at a temperature and water partial pressure effective to maintain a predetermined catalytic activity index, wherein the catalytic activity index is represented by the formula:

$CAI = \exp(f(T) * f(PP_{water})^n * alpha * t)$ wherein
t=time of contact of catalyst with water (hours)
T=temperature at contact (° C.)
$PP_{water}$=Partial Pressure of water in contact gas (psia)
alpha=−0.071
n=3.5
$f(T)=\exp(ea(1/(T+273)−1/(T_o+273)))$
ea=−5500° K
$T_o$=2000° C.
$f(PP_{water})$=(26.2*$PP_{water}$+1.14)*0.175, for T≧180° C. (453° K)
$f(PP_{water})$=((26.2+0.272*(180−T))*$PP_{water}$/$P_{sat}$+1.14) *0.175, for 180° C. (453° K)>T≧150° C. (433° K)
$P_{sat}$=Saturation pressure of water at T (psia).

2. The method of claim 1, wherein the activated metalloaluminophosphate molecular sieve is contacted with the gas at a temperature and water partial pressure effective to maintain a catalytic activity index of at least 0.7.

3. The method of claim 2, wherein the activated metalloaluminophosphate molecular sieve is contacted with the gas at a temperature and water partial pressure effective to maintain a catalytic activity index of at least 0.8.

4. The method of claim 3, wherein the activated metalloaluminophosphate molecular sieve is contacted with the gas at a temperature and water partial pressure effective to maintain a catalytic activity index of at least 0.9.

5. The method of claim 1, wherein the gas has a relative water pressure of at least 0.0001 and contacts the activated molecular sieve at a temperature less than water critical temperature.

6. The method of claim 5, wherein the gas has a relative water pressure of at least 0.001.

7. The method of claim 6, wherein the gas has a relative water pressure of at least 0.01.

8. The method of claim 7, wherein the gas has a relative water pressure of at least 0.1.

9. The method of claim 1, wherein the gas contacts the activated molecular sieve at a temperature of from 150° C. to 300° C.

10. The method of claim 1, wherein the activated metalloaluminophosphate molecular sieve is contacted with the gas for not greater than 500 hours.

11. The method of claim 10, wherein the activated metalloaluminophosphate molecular sieve is contacted with the gas from 0.01 hour to 50 hours.

12. The method of claim 1, wherein the activated metalloaluminophosphate molecular sieve is a silicoaluminophosphate molecular sieve.

13. The method of claim 1, further comprising stopping contact of the activated metalloaluminophosphate molecular sieve with the gas and storing in an anhydrous environment.

14. The method of claim 1, wherein the catalytic activity is catalytic activity in reaction processes selected from the group consisting of catalytic cracking, hydrocracking, dewaxing, olefin forming reactions, aromatics forming reactions, paraffin isomerization, olefin isomerization, paraffin hydroisomerization, olefin hydroisomerization, olefin oligonierization, olefin polymerization, reforming, alkylation, and disproportionation of aromatics.

15. The method of claim 1, wherein the activated molecular sieve is contacted so as to maintain an ethylene or propylene selectivity of at least 25 wt %.

16. A method of protecting catalytic activity of an activated metalloaluminophosphate molecular sieve in olefin forming reactions due to contact with water vapor, comprising contacting the activated metalloaluminophosphate molecular sieve with a gas for a time effective to maintain the activated metalloaluminophosphate molecular sieve at a catalytic activity index of at least 0.7 and at an ethylene or propylene selectivity of at least 25 wt %, wherein the gas is at a relative water pressure of from 0.0001 to 1.

17. The method of claim 16, wherein the gas contacts the activated molecular sieve at a temperature less than water critical temperature.

18. The method of claim 17, wherein the activated metalloaluminophosphate molecular sieve is contacted with the gas for a time effective to maintain a catalytic activity index of at least 0.8.

19. The method of claim 18, wherein the activated metalloaluminophosphate molecular sieve is contacted with the gas for a time effective to maintain a catalytic activity index of at least 0.9.

20. The method of claim 16, wherein the gas has a relative water pressure of at least 0.001.

21. The method of claim 20, wherein the gas has a relative water pressure of at least 0.01.

22. The method of claim 21, wherein the gas has a relative water pressure of at least 0.1.

23. The method of claim 16, wherein the gas contacts the activated molecular sieve at a temperature of from 150° C. to 300° C.

24. The method of claim 23, wherein the activated metalloaluminophosphate molecular sieve is contacted with the gas for not greater than 500 hours.

25. The method of claim 24, wherein the activated metalloaluminophosphate molecular sieve is contacted with the gas from 0.01 hour to 50 hours.

26. The method of claim 16, wherein the activated metalloaluminophosphate molecular sieve is a silicoaluminophosphate molecular sieve.

27. The method of claim 16, further comprising stopping contact of the activated metalloaluminophosphate molecular sieve with the gas and storing in an anhydrous environment.

28. A method of activating metalloaluminophosphate molecular sieve, the method comprising the steps of:
   a) providing a metalloaluminophosphate molecular sieve containing template;
   b) calcining the metalloaluminophosphate molecular sieve in a calcination unit to remove the template;
   c) sweeping gas through the calcination unit to cool the calcined metalloaluminophosphate molecular sieve, while maintaining the calcined metalloaluminophosphate molecular sieve at a catalytic activity index of at least 0.7, wherein the gas has a relative water pressure of at least 0.0001 and contacts the activated molecular sieve at a temperature less than water critical temperature.

29. The method of claim 28, wherein the activated metalloaluminophosphate molecular sieve is maintained at a catalytic activity index of at least 0.8.

30. The method of claim 29, wherein the activated metalloaluminophosphate molecular sieve is maintained at a catalytic activity index of at least 0.9.

31. The method of claim 28, wherein the gas has a relative water pressure of at least 0.001.

32. The method of claim 31, wherein the gas has a relative water pressure of at least 0.01.

33. The method of claim 32, wherein the gas has a relative water pressure of at least 0.1.

34. The method of claim 28, wherein the gas is at a temperature of from 150° C. to 300° C.

35. The method of claim 28, wherein the gas is swept through the calcination unit for not greater than 500 hours.

36. The method of claim 35, wherein the gas is swept through the calcination unit from 0.01 hour to 50 hours.

37. The method of claim 28, wherein the activated metalloaluminophosphate molecular sieve is a silicoaluminophosphate molecular sieve.

38. The method of claim 28, further comprising removing the activated metalloaluminophosphate molecular sieve from the calcination unit and storing the removed molecular sieve in an anhydrous environment.

39. The method of claim 28, wherein the catalytic activity is catalytic activity in reaction processes selected from the group consisting of catalytic cracking, hydrocracking, dewaxing, olefin forming reactions, aromatics forming reactions, paraffin isomerization, olefin isomerization, paraffin hydroisomerization, olefin hydroisomerization, olefin oligomerization, olefin polymerization, reforming, alkylation, and disproportionation of aromatics.

40. The method of claim 28, wherein the activated molecular sieve is contacted with the gas so as to maintain an ethylene or propylene selectivity of at least 25 wt %.

41. A method of protecting catalytic activity of an activated metalloaluminophosphate molecular sieve in olefin forming reactions due to contact with water vapor, comprising contacting the activated metalloaluminophosphate molecular sieve with a gas containing water to effectively maintain the activated metalloaluminophosphate molecular sieve at a predetermined catalytic activity index, wherein the activated metalloaluminophosphate molecular sieve contains Si and Al at a Si/Al ratio of not greater than 0.5.

42. The method of claim 41, wherein the activated metalloaluminophosphate molecular sieve contains Si and Al at a Si/Al ratio of not greater than 0.3.

43. The method of claim 42, wherein the activated metalloaluminophosphate molecular sieve contains Si and Al at a Si/Al ratio of not greater than 0.2.

44. The method of claim 43, wherein the activated metalloaluminophosphate molecular sieve contains Si and Al at a Si/Al ratio of not greater than 0.15.

45. The method of claim 44, wherein the activated metalloaluminophosphate molecular sieve contains Si and Al at a Si/Al ratio of not greater than 0.1.

46. The method of claim 41, wherein the metalloaluminophosphate molecular sieves contain Si and Al at a ratio of at least 0.005.

47. The method of claim 46, wherein the metalloaluminophosphate molecular sieves contain Si and Al at a ratio of at least 0.01.

48. The method of claim 47, wherein the metalloaluminophosphate molecular sieves contain Si and Al at a ratio of at least 0.02.

49. A method of protecting activated metalloaluminophosphate molecular sieve from loss of catalytic activity, comprising contacting the activated metalloaluminophosphate molecular sieve with a gas containing water at a temperature above water critical temperature.

* * * * *